United States Patent [19]

Pounds

[11] 4,441,486
[45] Apr. 10, 1984

[54] HYPERTHERMIA SYSTEM

[75] Inventor: Douglas W. Pounds, Menlo Park, Calif.

[73] Assignee: Board of Trustees of Leland Stanford Jr. University, Stanford, Calif.

[21] Appl. No.: 315,579

[22] Filed: Oct. 27, 1981

[51] Int. Cl.³ .............................................. A61B 5/00
[52] U.S. Cl. .................................................. 128/24 A
[58] Field of Search .................. 128/24 A, 660, 804; 367/138; 310/334

[56] References Cited

U.S. PATENT DOCUMENTS

| | | |
|---|---|---|
| 2,407,690 | 9/1946 | Southworth . |
| 2,559,227 | 7/1951 | Rieber . |
| 3,237,623 | 3/1966 | Gordon . |
| 3,387,604 | 6/1968 | Erikson . |
| 3,499,437 | 3/1970 | Balamuth . |
| 3,825,887 | 9/1974 | Murray ............................ 367/138 |
| 3,828,769 | 8/1974 | Mettler . |
| 3,941,122 | 3/1976 | Jones . |
| 3,991,770 | 10/1976 | Leveen . |
| 4,016,886 | 4/1977 | Doss et al. . |
| 4,032,860 | 6/1977 | Leveen . |
| 4,216,766 | 8/1980 | Duykers et al. . |

OTHER PUBLICATIONS

Doss and McCabe, "A Technique for Localized Heating in Tissue: An Adjunct to Tumor Therapy," Medical Instrumentation, vol. 10, No. 1, Jan.-Feb. 1976, pp. 16-21.

Lele, "Hyperthermia by Ultrasound," Massachusetts Institute of Technology Industrial Liaison Program, Feb. 7, 1976.

Hahn and Pounds, "Heat Treatment of Solid Tumors: Why and How," Applied Radiology, Sep.-Oct., 1976, pp. 131-144.

Li and Hahn, "Cellular Inactivation by Ultrasound," Nature, vol. 267, May 12, 1977, pp. 163-165.

Gerner et al., "The Potential of Localized Heating as an Adjunct to Radiation Therapy," Radiology, vol. 116, Aug. 1975, pp. 433-439.

Primary Examiner—Richard J. Apley
Assistant Examiner—David J. Brown
Attorney, Agent, or Firm—Townsend and Townsend

[57] ABSTRACT

An ultrasonic hyperthermia system capable of producing discrete heating of a volume of deep-seated, normally perfused tissue. An individual transducer is configured and driven so that its compressional mode of vibration is suppressed near the center, with the result that the near field is characterized by the substantial absence of a strong central (on-axis) peak. This is preferably accomplished by driving the transducer at a frequency such that the transverse mode of vibration is responsible for the suppression. The near field transverse intensity distribution is further characterized by an annular satellite peak that surrounds the axis. As one proceeds axially away from the transducer, the satellite peak decreases and a predominant central peak occurs. A plurality of transducers are mounted in an isospherical configuration so that the corresponding plurality of beams are directed toward a central axis of the system. Simultaneous heating of a relatively large cylindrical region is achieved in a system wherein the beams do not actually cross one another, but rather are offset with respect to the central axis. As the beams approach each other, portions of their satellite peaks add to heat the central portion of the cylindrical region while the central peaks heat the outer portion. In the region where the beams converge, the central peaks concentrate the power within the heated cylindrical region.

19 Claims, 17 Drawing Figures

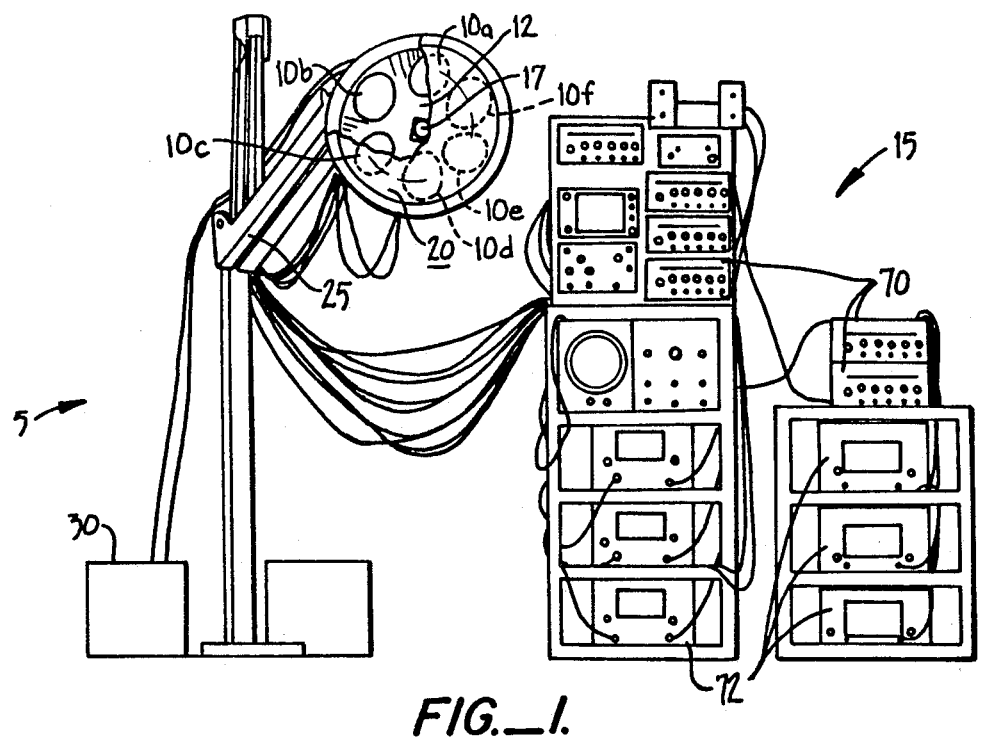
FIG._1.
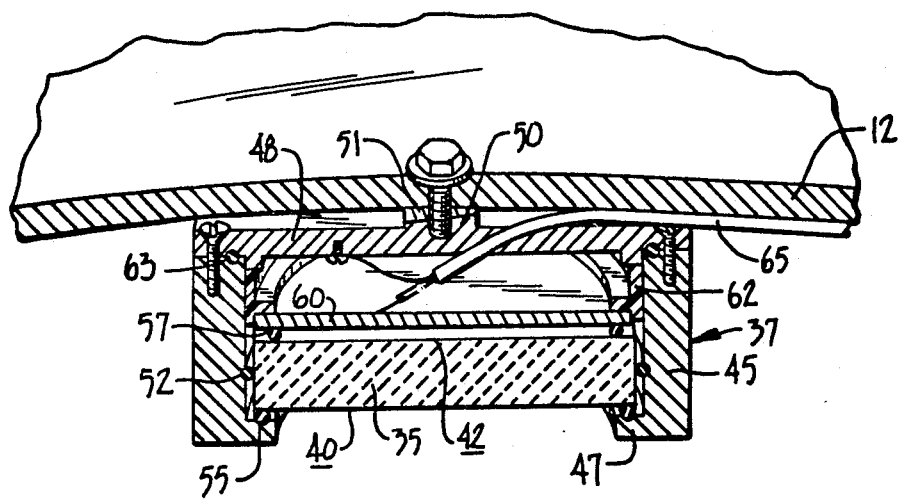
FIG._2.

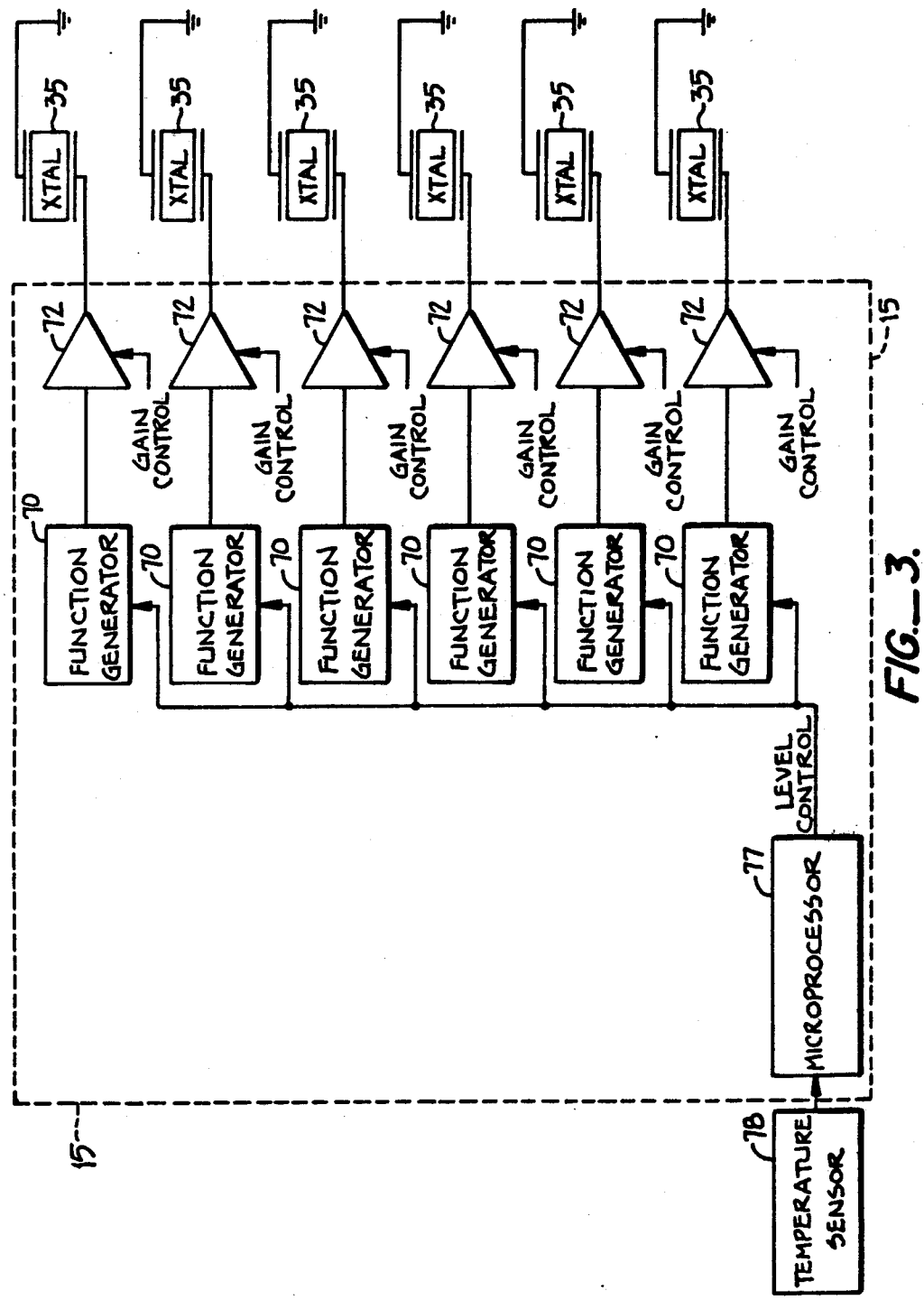
FIG._3.

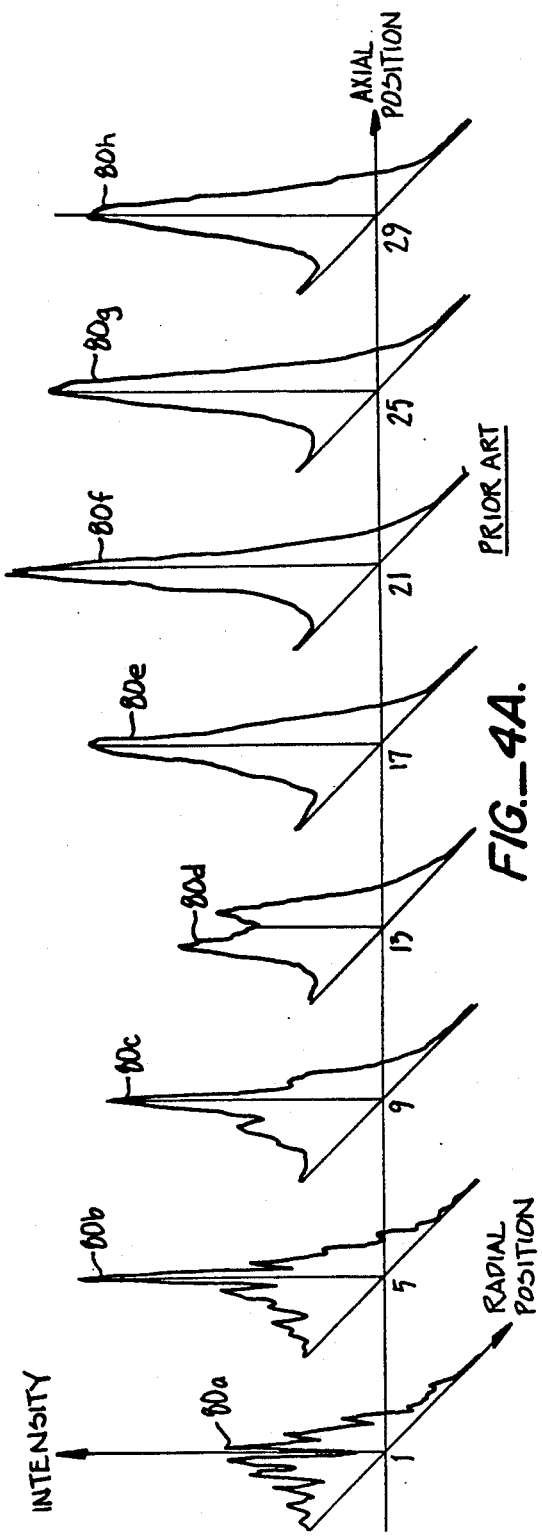
FIG._4A. PRIOR ART
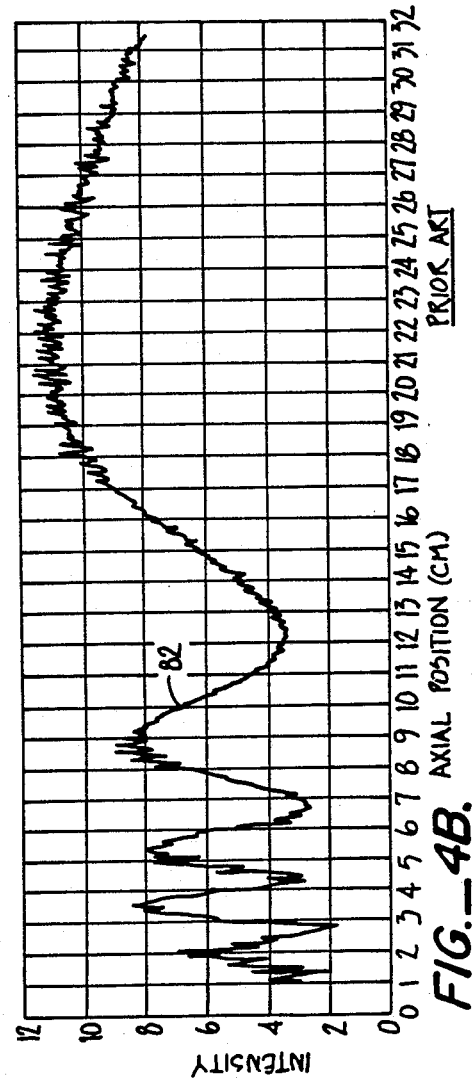
FIG._4B. PRIOR ART

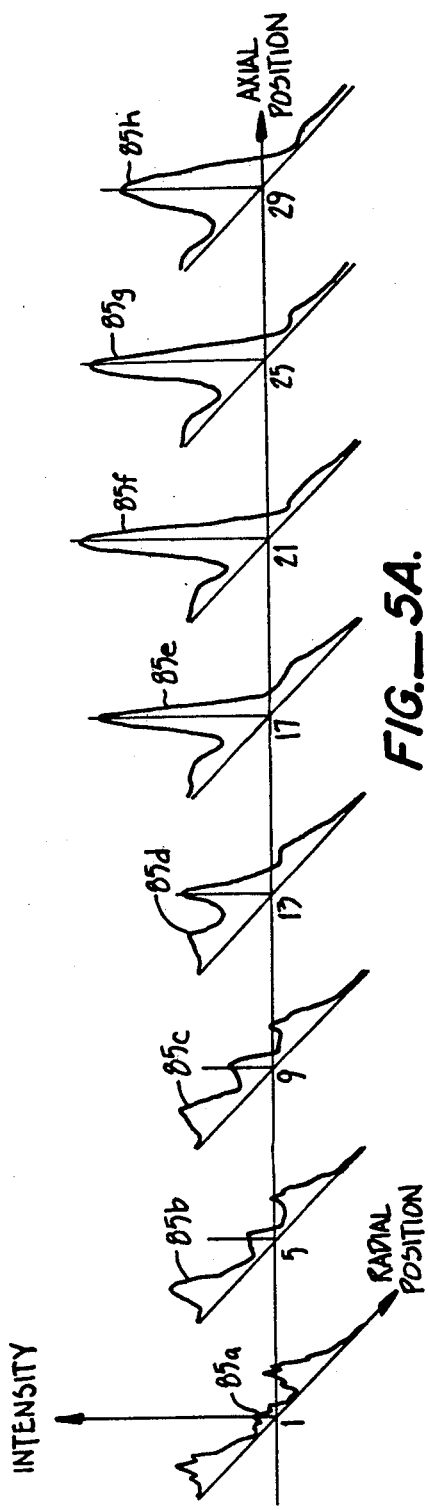
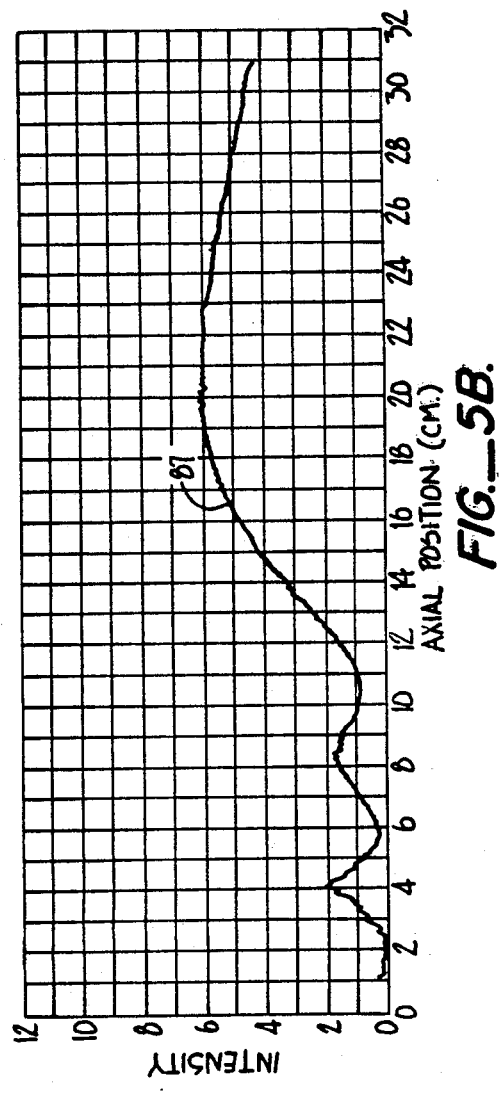
FIG.—5A.
FIG.—5B.

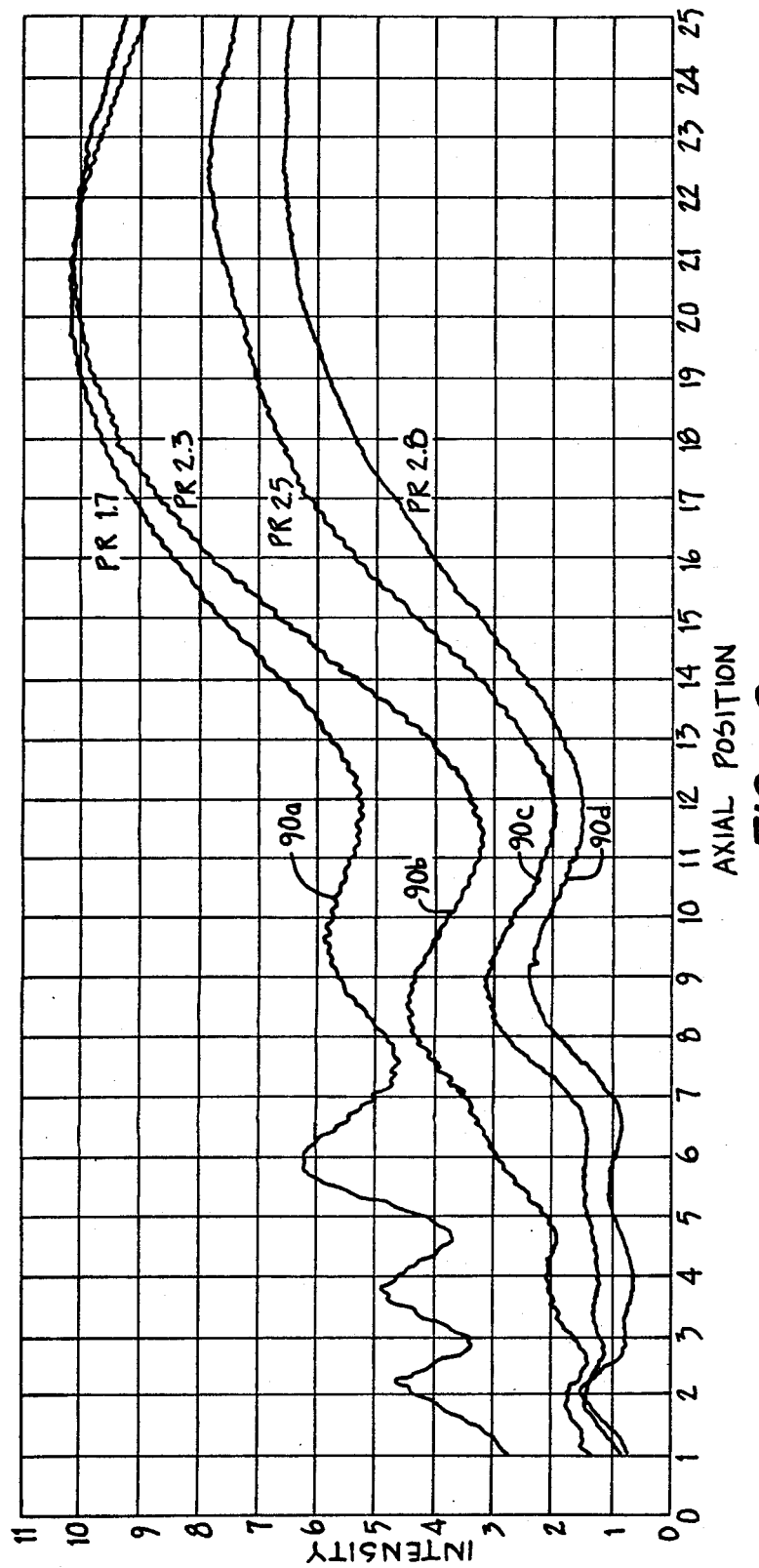
FIG._6.

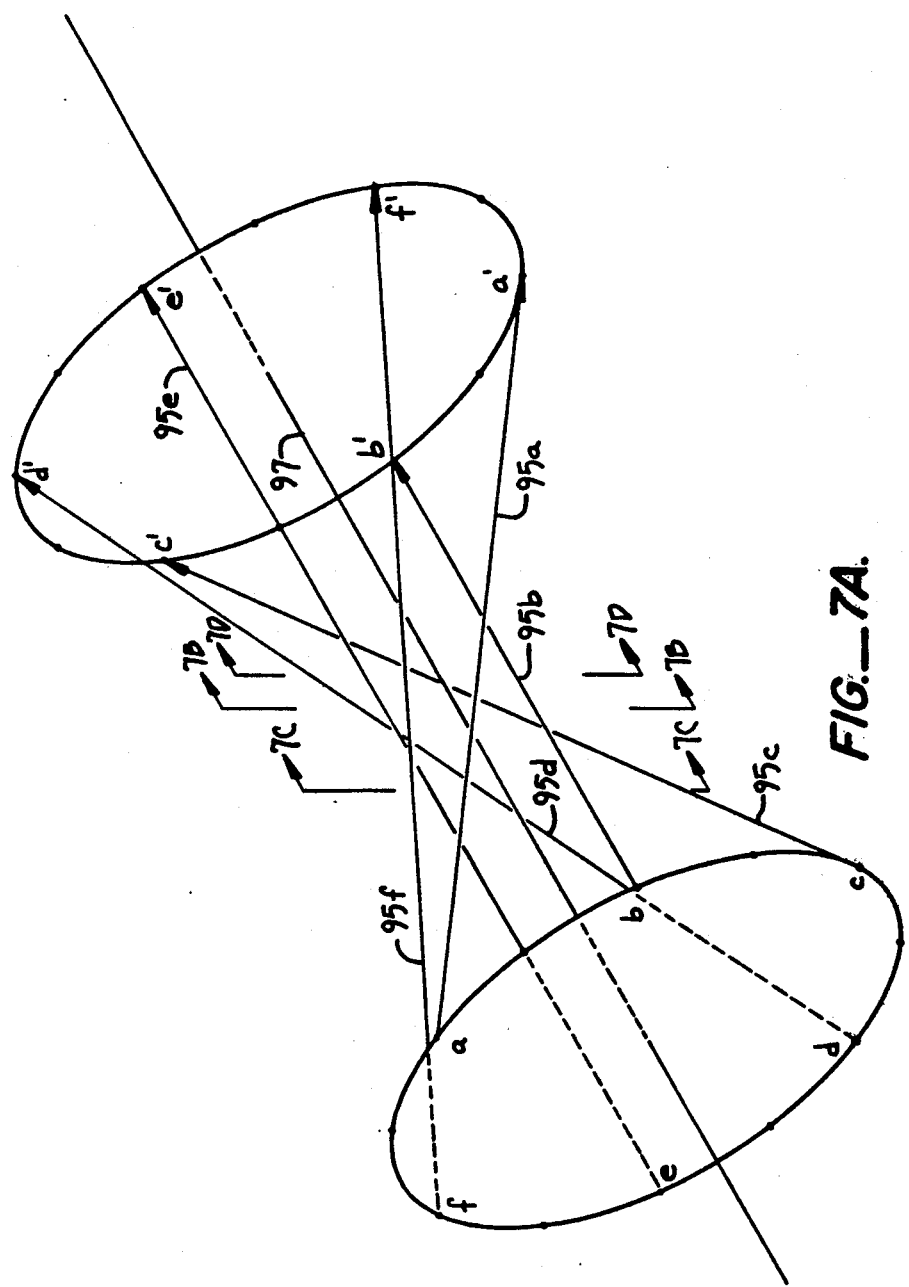
FIG._7A.

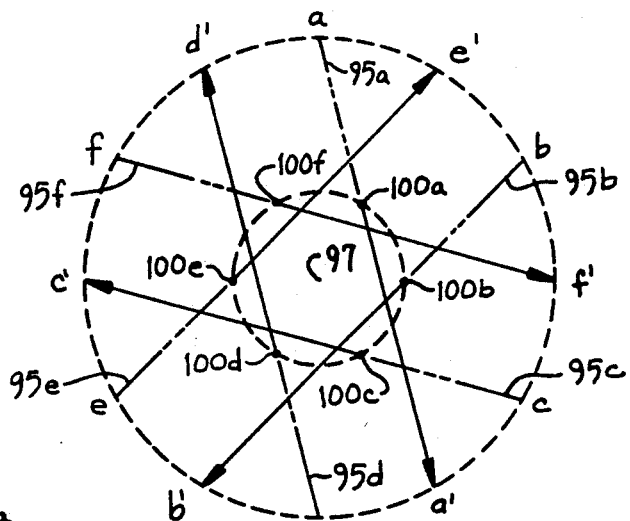
FIG._7C.
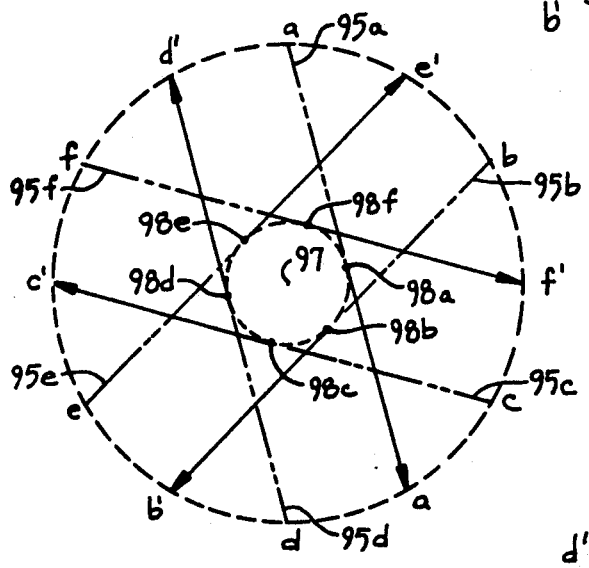
FIG._7B.
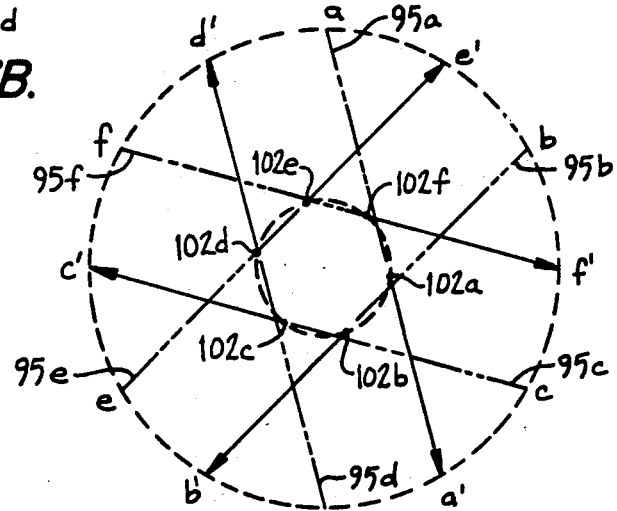
FIG._7D.

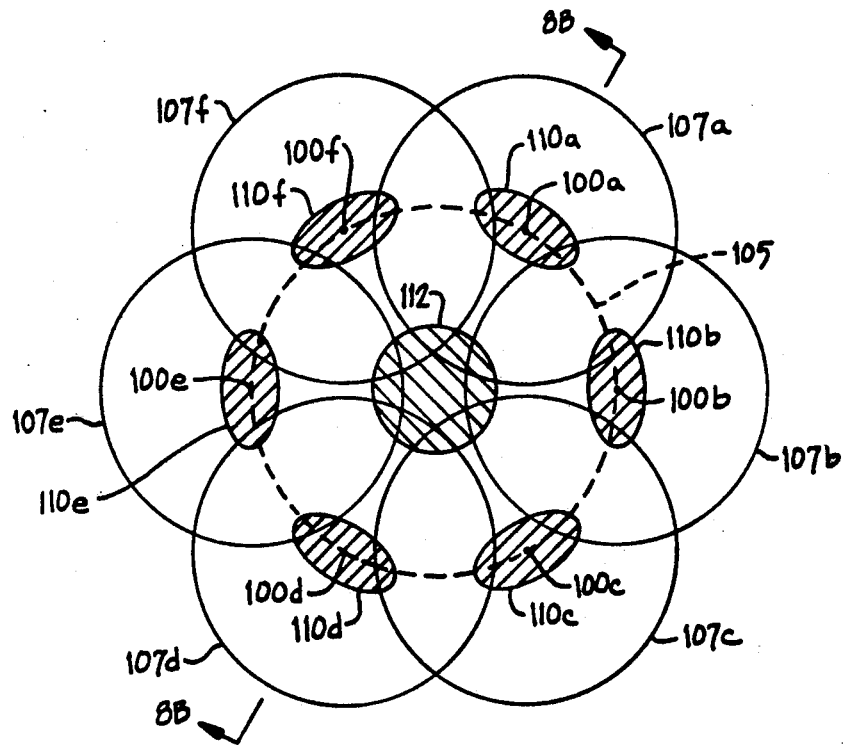
FIG._8A.
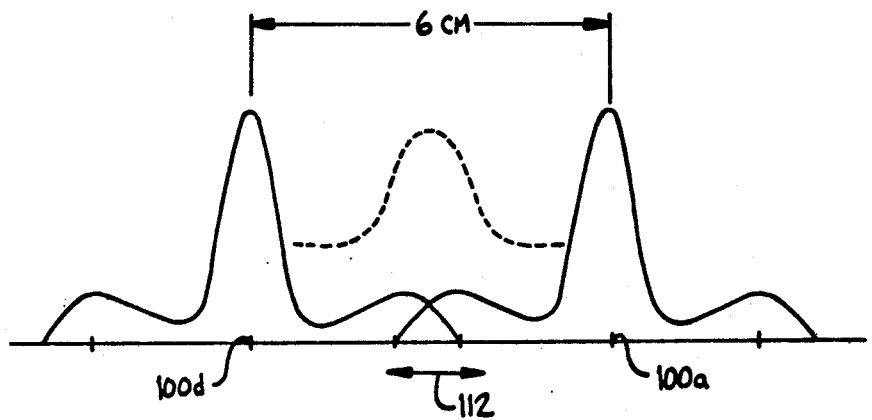
FIG._8B.

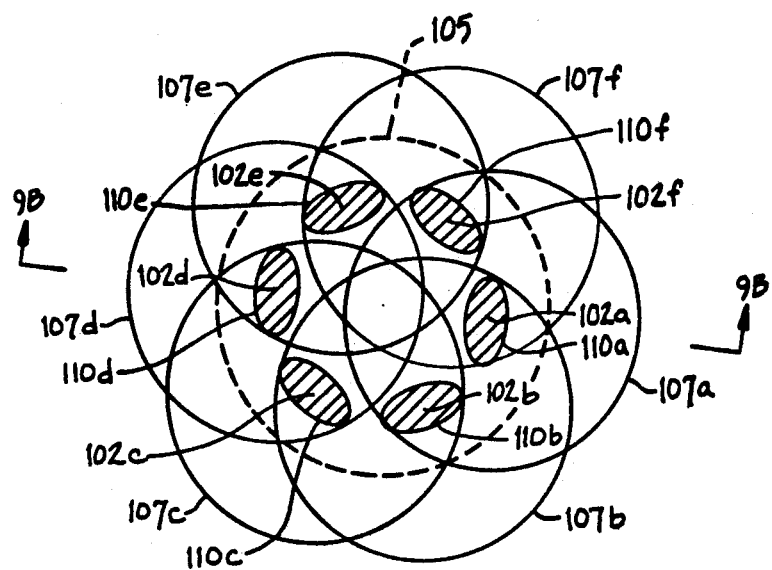
FIG._9A.
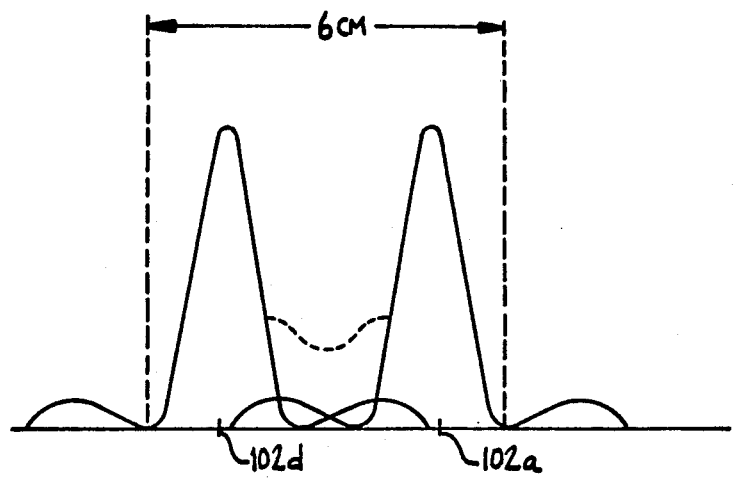
FIG._9B.

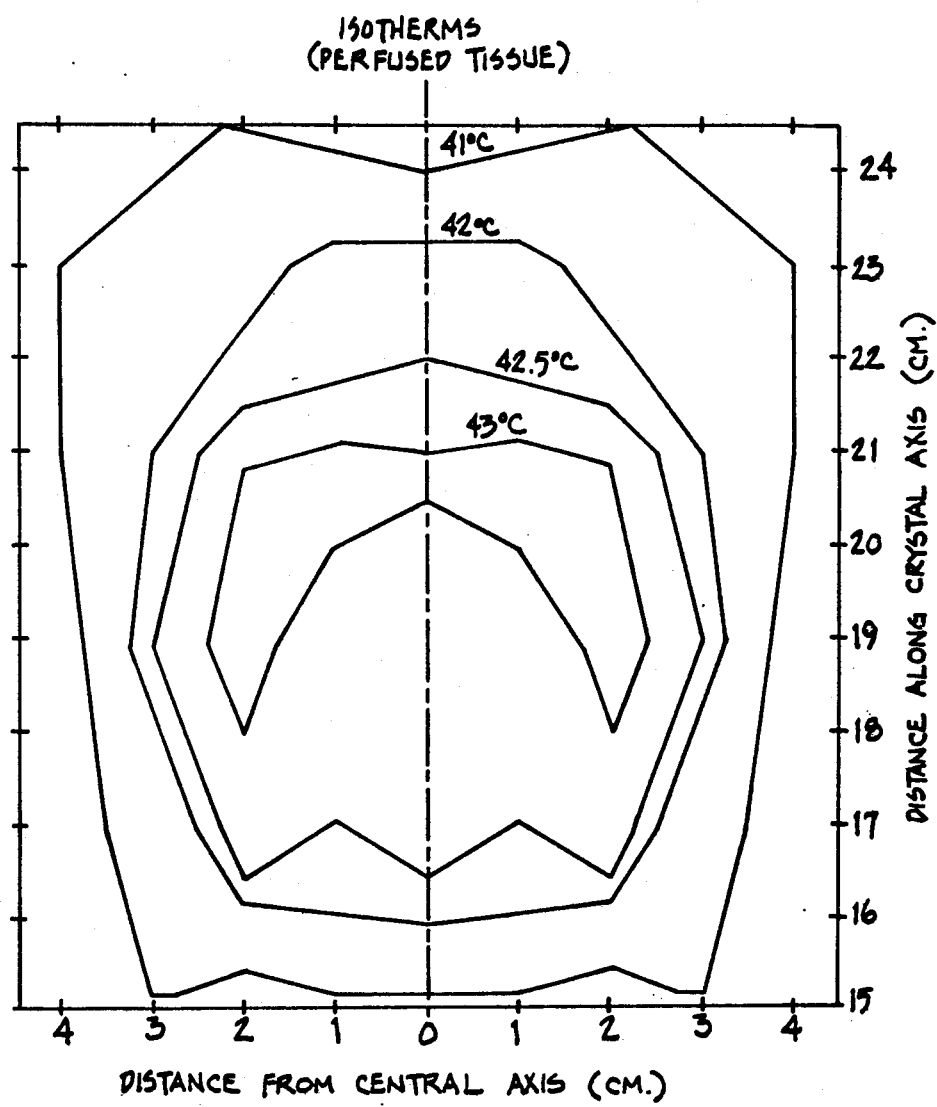
FIG._10.

HYPERTHERMIA SYSTEM

FIELD OF THE INVENTION

The present invention relates generally to ultrasonic transducers, and more specifically to a system for effecting hyperthermia by means of ultrasonic radiation.

BACKGROUND OF THE INVENTION

In recent years, there has been increasing interest in the use of heat treatment (hyperthermia) for controlling or preventing the growth of malignant cells. While hyperthermia has some demonstrated utility as a stand-alone modality, it shows most promise when used as an adjunct therapy in combination with other treatments such as ionizing radiation or chemotherapy. In both patient and animal testing, it has been found that heating tumors to temperatures in the range of 41°–45° C. can reduce at least 50% of tumor masses in at least 50% of the subjects treated. Although the reason for this is not yet well understood, it appears that malignant cells are inherently more sensitive to heat than normal cells, and furthermore that the thermal sensitivity of cells in poorly perfused regions (such as solid tumors) is increased. It is also noted that where the tumor is poorly perfused, it is easier to induce local hyperthermia.

The use of ultrasound to induce hyperthermia is well-known, and the basic method of ultrasonic treatment is generally as follows. An ultrasonic transducer is acoustically coupled to the subject's skin, taking care to avoid an air-tissue interface which would cause reflection. The transducer is electrically driven at a frequency of several hundred kilohertz which causes pressure waves to propagate into the tissue. The tissue becomes heated by the dissipation of the ultrasonic pressure waves. The intensity distribution associated with the waves is characterized by a prominant central (on-axis) peak. The heat generated in the tissue is a function of the time averaged intensity distribution of the pressure waves and further depends on such factors as the perfusion of the tissue.

As is well known in the art, there are other methods of inducing local hyperthermia, namely microwave radiation, and induced radiofrequency current heating (either directly applied or electromagnetically induced), but ultrasonic techniques have certain advantages. More particularly, the ultrasonic transducers may be constructed to permit scanning and to provide well-collimated beams which can be easily focused and manipulated. Additionally, ultrasound is not associated with biohazard and does not interfere with temperature measurements which are necessary to control the hyperthermia treatment. Moreover, ultrasound does not preferentially heat fatty tissue, although it is noted that bone has an appreciably higher rate of absorption.

However, to date, ultrasonic treatment has been largely restricted to depths of at most a few centimeters, and attempts to deliver usable amounts of power to greater depths (for example, 15 cm) have tended to result in unacceptable overheating of the surface and near surface tissue. Moreover, systems for treating the shallow regions have been plagued by phase interference effects. Therefore, in spite of the great promise shown by the use of ultrasonically induced hyperthermia for tumor treatment, the range of applications has been limited so that the full potential of the treatment has not been realized.

SUMMARY OF THE INVENTION

The present invention provides an ultrasonic hyperthermia system capable of producing discrete heating of a volume of deep-seated, normally perfused tissue, thus rendering possible the heat treatment of deep-seated tumors without appreciable heating of the surrounding or intervening tissues. Broadly, this is accomplished by acoustically coupling a transducer to the subject's skin, and configuring and driving the transducer so that its compressional mode of vibration is suppressed near the center, with the result that the near field is characterized by the substantial absence of a strong central (on-axis) peak. This is preferably accomplished by driving the transducer at a frequency such that the transverse mode of vibration is responsible for the suppression. The near field transverse intensity distribution is further characterized by an annular satellite peak that surrounds the axis. As one proceeds axially away from the transducer, the satellite peak decreases and a predominant central peak occurs. The transition distance, that is, the distance at which the central peak becomes predominant may be controlled by changing the diameter of the transducer crystal or the frequency at which it is driven. The suppression of the near field central peak is achieved without decreasing the cross-sectional area of the far field central peak (as would occur by merely focusing the beam).

According to a further aspect of the present invention, a plurality of transducers are mounted in an isospherical configuration so that the corresponding plurality of beams are directed toward a central axis of the system. The separation of the transducer and the angle of inclination are such that the beams approach one another in a region that includes their respective points of maximum intensity. That is, assuming that the transducers are characterized by generally equal transition distances, the region of convergence is at a distance generally equal to the transition distance. Simultaneous heating of a relatively large cylindrical region is achieved in a system wherein the beams do not actually cross one another, but rather are offset with respect to the central axis. As the beams approach each other, portions of their satellite peaks add to heat the central portion of the cylindrical region while the central peaks heat the outer portion. In the region where the beams converge, the central peaks concentrate the power within the heated cylindrical region. As the beams diverge, the satellite peaks have largely vanished, the beams individually and collectively diverge, and this effect, coupled with attenuation produces a rapid falloff in power density per unit volume.

For a further understanding of the nature and advantages of the present invention, reference should be made to the remaining portions of the specification and to the attached drawings.

BRIEF DESCRIPTION OF THE DRAWINGS

FIG. 1 illustrates in schematic form an ultrasonic hyperthermia system according to the present invention;

FIG. 2 is a sectional oblique view illustrating the preferred transducer mounting;

FIG. 3 is an electrical block diagram of a system according to the present invention;

FIGS. 4A and 4B illustrate the intensity pattern for a transducer operated according to the prior art;

FIGS. 5A and 5B illustrate the intensity pattern for a transducer operated according to the present invention;

FIG. 6 illustrates a family of intensity curves generated during the calibration of a transducer according to the present invention;

FIGS. 7A-D illustrate the orientation of the transducer axes;

FIGS. 8A and 8B illustrate the intensity distribution resulting from multiple beams as they approach one another;

FIGS. 9A and 9B illustrate the intensity distribution resulting from multiple beams as they pass through the region slightly beyond their convergence point; and FIG. 10 is the temperature distribution in normally perfused muscle for multiple beams.

DETAILED DESCRIPTION OF THE INVENTION

Basic Structure

FIG. 1 is a partially cut away drawing illustrating an ultrasonic hyperthermia system 5 according to the present invention. The purpose of system 5 is to induce hyperthermia (heating) in selected portions of a subject tissue volume. Broadly, the system includes a plurality of piezoelectric transducers 10a-f (designated collectively as transducers 10) which are mounted to a concave alignment plate 12 and driven by high frequency driving circuitry 15. Transducers 10 are mounted to plate 12 which holds them in relative alignment with their respective axes inclined with respect to a central axis. The individual transducer axes (and hence the ultrasonic beams) are thus directed into a common region located within the subject tissue volume. Depending on the application, the transducer axes may be directed so as to actually intersect the central axis, or may be directed to pass within a short distance thereof without actually intersecting. The system described herein is characterized by an angle of about 30° between each transducer axis and the central axis.

Alignment plate 12 also carries a centrally mounted ranging transducer 17 which is coupled to a standard ranging system such as a Hewlett-Packard echoencephaloscope, Model No. 7215A. The particular ranging system is not part of the present invention, and will not be described further. A thin flexible membrane 20 maintains a body of water in contact with transducers 10 to allow acoustic coupling to the subject tissue volume. The assembly comprising alignment plate 12, transducers 10, membrane 20, and the volume of water is itself supported by an appropriate positioning fixture 25. The system also includes a water circulation and degassing system 30.

FIG. 2 is a sectioned oblique view illustrating in detail one of transducers 10. Transducer 10 includes a piezoelectric crystal 35 mounted within an aluminum housing 37 which is itself mounted to alignment plate 12. Crystal 35 is of generally cylindrical configuration, a 7.5-cm diameter and 1-cm thickness being typical. Crystal 35 is shown as having flat faces, although the present invention may be used with focused beams, in which case the front face could be concave. A preferred crystal material is lead zirconium titanate (PZT-8). Suitable crystals may be obtained from Speciality Engineering, Santa Clara, California. Crystal 35 is conductively plated on its end faces to define a front electrode 40 and a rear electrode 42, with front electrode 40 being in contact with the water and rear electrode 42 being within housing 37. Housing 37 has a cylindrical sidewall 45, a front annular flange 47 carried thereon, and a rear circular wall 48. Wall 48 carries has a raised central mounting pad 50 which is bolted to alignment plate 12. A tapered washer 51 is interposed between mounting pad 50 and alignment plate 12 to permit the transducer axis to be oriented as desired relative to the central axis. Mounting pad 50 may be provided with a complementary taper to permit an orientation with the transducer axis perpendicular to alignment plate 12 (as shown).

The internal dimensions of housing 37 are such to provide a radial clearance between the inner housing surface and the outer surface of crystal 35, this clearance being maintained by an insulative 0-ring 52. A first conductive 0-ring 55 is interposed between front electrode 40 and annular flange 47 while a second conductive 0-ring 57 is interposed between rear electrode 42 and a circular conducting plate 60 which may be copper or brass. An insulating sleeve 62 prevents conducting plate 60 from contacting housing 37. The axial dimensions of crystal 35 and housing 37 are such that conductive 0-rings 55 and 57 are in compression to provide a good electrical contact between front electrode 40 and housing 37 and between rear electrode 42 and copper plate 60, and further to provide a liquid-tight seal at 0-ring 55. An 0-ring 63 maintains a liquid-tight seal between sidewall 45 and rear wall 48 of housing 37.

High frequency electrical power is communicated to crystal 35 via a coaxial cable 65, the ground shield of which is connected to housing wall 48 (which is itself electrically connected to the remaining portions of housing 37 and thus to front electrode 40) while the central signal conductor is electrically connected to copper plate 60 (which is connected to rear electrode 42). Coaxial cable 65 passes through housing wall 48 at a relatively shallow angle to avoid kinking the cable. The penetration is sealed with RTV rubber or the like.

FIG. 3 is an electrical block diagram of electrical driving circuitry 15. Each crystal 37 has an associated function generator 70 and amplifier 72. Function generator 70 produces a high frequency output at a frequency appropriate for its particular crystal, and modulates this frequency over a narrow range (±2 kHz) in order to average out the effects of crystal imperfections. The determination of appropriate frequencies is a key feature of the present invention, and will be discussed below. The output of function generator 70 is amplified by amplifier 72 which may be a standard RF power amplifier such as those made by Electronic Navigation Instruments (Model No. 240L).

The function generators receive a common level control signal on a line 75 which may be provided by manual setting, or preferably as an output signal from a microprocessor 77 which controls the operation of the system. Microprocessor 77 has an input responsive to a signal from a temperature sensor 80 which may be placed within the subject volume in order to provide closed loop operation. Each of amplifiers 72 is provided with its own separate gain control to allow each amplifier to be tuned for its respective crystal's efficiency and other characteristics. The common level control then allows the overall output power of the system to be varied while the relative contributions of the individual transducers remains the same. Table 1 sets forth the nominal frequencies and rms voltage level supplied to the transducers in a typical system. It is to be understood that the particular frequencies are for particular transducers, and must be determined as will be described below), while the rms voltages exhibit a variation that reflects the variations among the individual crystals.

TABLE 1

| Frequency (kHz) | RMS Voltage |
| --- | --- |
| 369 | 62 |
| 365 | 77 |
| 367 | 62.5 |
| 353 | 82 |
| 370 | 52 |
| 352 | 72.5 |

As will be described below, the present invention is primarily drawn to the manner in which transducers 10 are driven to produce an intensity distribution that allows substantial power deposition at considerable depths without appreciable heating of the intervening tissues, and to the manner in which the intensity distributions of the individual transducers are caused to cooperate with one another to provide heating of a discrete volume of deep-seated tissue.

Single Transducer Operation

Prior to describing the operation of the entire system having the plurality of transducers, it is important to fully understand the effect of a given single transducer. As is well known, the application of a high frequency voltage across electrodes 40 and 42 causes axial vibrations of crystal 35, thus causing ultrasonic pressure waves to be propagated axially outward from the crystal to any acoustically coupled medium (the water and the subject tissue volume). These ultrasonic pressure waves are dissipated in the tissue volume and cause heating thereof. The particular temperature distribution will be correlated with the intensity distribution, taking into effect such phenomena as thermal conductivity and perfusion. Normally, the frequency of operation is chosen relative to the thickness of the crystal and the sonic velocity in the crystal to provide resonant operation in order to maximize the amount of vibrational energy in the crystal that is delivered to the subject tissue volume. The discussion that follows is with reference to a system in which the beam is not focused. It is to be understood, however, that the present invention may be used in conjunction with lenses and the like, should it be desired.

FIGS. 4A and 4B show a typical intensity pattern arising from a crystal operated in the normal (prior art) fashion. While the intensity pattern varies in three dimensions, it is cylindrically symmetrical about the transducer axis, and the main features may be conveniently displayed by a longitudinal distribution and a family of transverse distributions. FIG. 4A shows the family of transverse distribution curves 80a–h showing intensity as a function of (radial) distance from the transducer axis, with each curve being drawn for a particular (axial) distance from the crystal face. FIG. 4B is a longitudinal distribution curve 82 showing the on-axis intensity at a given axial distance as a function of axial distance. As can be seen, the transverse intensity distributions near the transducer are qualitatively different from those far removed therefrom. It is customary to define a so-called "transition distance" which corresponds to the point of last maximum on the longitudinal distribution. The region that is less than the transition distance from the transducer is called the near field region; that beyond the transition distance is called the far field. For the particular transducer illustrated, the transition distance is around 20 cm. It is, of course, to be understood that these dimensions are strongly dependent on the crystal geometry and operating characteristics, and that the values are representative only. Moreover, the distance to the last peak would be slightly different if attenuation (to be discussed below) were taken into account.

The transverse distributions in the far field are characterized by the presence of a very strong and well-defined central peak having a full width at half maximum (FWHM) of about ¼ the crystal diameter. The transverse distributions in the near field, on the other hand, are typically rather ragged (rapid fluctuations as a function of radial coordinate). The near field distributions also show their greatest intensities near the axis, although the on-axis intensity shows a pronounced dip at some axial coordinates. In the near field, the longitudinal intensity distribution exhibits undulations representing alternating regions of high and low intensity while in the far field the longitudinal distribution is characterized by a more uniform high intensity which falls off at large distances.

The presence of the high intensity regions in the near field limits the amount of power which can be deposited in deep regions of the subject tissue volume, since attempts to heat a deep-seated tumor would cause undue heating of the shallow tissue. In this regard, the power ratio, defined as the ratio of maximum intensities in the far and near fields, is a useful parameter for comparison purposes. A high power ratio would indicate an ability to heat portions of the far field without unduly heating the intervening near field region. The power ratio for the longitudinal distribution of FIG. 4B is 1.3.

The corresponding transverse and longitudinal distributions for a crystal operated according to the present invention are shown in FIGS. 5A and 5B. The transverse distribution curves 85a–h of FIG. 5A differ from those of FIG. 4A in two main respects. The first, and most significant, is that the central peak is strongly suppressed in the near field. The second is that there appears a satellite peak at about ½–⅔ the crystal radius. This satellite peak represents an enhanced intensity within an annular region about the axis. The satellite peak dominates the central peak over most of the near field region, and persists, albeit in attenuated form, into the far field. The longitudinal distribution curve 87 exhibits similar qualitative behavior to that of FIG. 4B, although the near field undulations are fewer in number. The major difference is quantitative, and is one of the key features of the present invention—the power ratio is much higher, in this case 3.0.

It is noted that the absolute intensity levels in FIGS. 5A and 5B are lower than those in FIGS. 4A and 4B, both sets of curves representing operation at the same input voltage level. This does not represent a significant drawback, since the input voltage may be increased to achieve a desired intensity level in the far field, and heating of the near field tissue regions is avoided.

FIG. 6 is a plot illustrating the manner in which the correct operating frequency is determined. Broadly, the present invention achieves the results exemplified in the plot of FIGS. 5A and 5B by the suppression of compressional mode vibrations near the center of the crystal. The technical explanation set forth below represents the present understanding of the preferred suppression mechanism, and while other effects may be operating, the observed behavior is consistent with this explanation.

As discussed above, the application of a voltage between the spaced parallel electrode surfaces causes axial compression (or expansion) of the crystal. However, as the axial dimension of the crystal changes in response to the impressed voltage, corresponding radial deformation occurs. Thus, when the crystal expands axially, it shrinks radially; when it compresses axially, it expands radially. Thus, the compressional and transverse modes of vibration are coupled, and the excitation of the compressional modes causes excitation of transverse modes. While these transverse modes of vibration do not propagate into the subject tissue volume, they have an important effect on the compressional modes that do. More particularly, the crystal diameter and operating frequency are chosen so that during the portion of the cycle when acoustic coupling to the subject tissue volume is maximum (maximum velocity of the compressional mode), the compressional and electrical effects of the transverse mode are caused to inhibit the output of the compressional mode near the crystal center.

As a general matter, the crystal thickness, sonic velocity, and operating frequency are related so that operation is at or near a resonant condition where the thickness is a half odd integral number of wavelengths (typically one half wavelength). This maximizes the transformation of electrical input energy into acoustical (ultrasonic) energy delivered to the subject tissue volume. By suitably selecting the crystal diameter and operating frequency, the suppression of the near field peaks may be achieved, and the transition distance may be set at a particular desired value. In order to make the determination, the transverse velocity within the crystal must be determined experimentally (if not known), at which point the frequency and diameter may be chosen in order to achieve the suppression in view of the properties of the transverse mode vibrations. However, the final determination is still done empirically.

FIG. 6 shows four longitudinal distributions, designated 90a-d, for the same crystal being driven at 342 kHz, 344 kHz, 346 kHz, and 348 kHz, respectively. The voltage in all four cases is the same (28 volts peak-to-peak into a 50 ohm load). The resonant frequency in this case is in the neighborhood of 338 kHz. As can be seen, increasing the frequency beyond the resonant frequency causes the overall intensity (as measured on the vertical axis) to fall off, but has the beneficial result that the fall-off of peak intensity in the near field is more rapid than that in the far field region. More particularly, while plot 90a represents a situation similar to that illustrated in FIGS. 4A and 4B, plot 90d represents a situation approaching that illustrated in FIGS. 5A and 5B. For plots 90a-d, the power ratios are 1.7, 2.3, 2.5, and 2.8, respectively (the corresponding power ratios for the plots in FIGS. 4A and 5A are 1.3 and 3.0). Power ratios of 5.0 or more are readily obtained.

The resonance requirement puts a constraint on the crystal thickness while the central suppression requirement puts a constraint on the crystal diameter. While in principle both requirements may be simultaneously realized, as a practical matter, the crystal is likely to have to be driven at a frequency off resonance (either higher or lower). Naturally, the farther off resonance the crystal is driven, the lower the efficiency of conversion from electrical energy to ultrasonic energy in the subject tissue volume. Within limits, if it is determined that the optimum intensity distribution requires operation significantly off resonance, suitable intensity in the subject tissue volume may be maintained by increasing the power input to the crystal. Conversely, the transducer may be driven at a frequency that sacrifices to some extent the power ratio in favor of higher conversion efficiency.

Multiple Transducer Operation

Having discussed the operation with respect to the individual transducers, the overall system operation may now be understood. The discussion that follows in connection with FIGS. 7A-D, 8A-B, 9A-B, and 10 is for beam orientations designed to heat a substantial region of deep tissue.

FIG. 7A is a schematic isometric view illustrating the orientation of the transducer axes for a configuration where the transducer axes do not cross each other or the central axis. For definiteness, the transducer axes are designated 95a-f while the central axis is designated 97. Axis 95a also is shown as axis a—a, axis 95b as b—b, and so on. The orientation is such that axes 95a-f make their closest approach to central axis 97 at the transition distance, say 20 cm. A typical distance of closest approach (offset) is about 1.5 cm, but in the drawings the offset is somewhat exaggerated. It should be noted that the transition distance does not represent a point of abrupt change in the intensity pattern. Therefore, the point of closest approach of the beams to the central axis need not be precisely at the transition distance.

FIGS. 7B, 7C, and 7D are transverse sections taken in planes perpendicular to central axis 97. FIG. 7B shows the points of intersection 98a-f of axes 95a-f with the plane at 20 cm wherein axes 95a-f make their closest approach to central axis 97 at points 98a-f. FIG. 7C shows the points of intersection 100a-f of axes 95a-f with the plane at about 15 cm wherein the beams (axes) are still converging. FIG. 7D shows the points of intersection 102a-f with the plane at about 22 cm wherein the beams (axes) are diverging.

The significance of the beam positions at the planes of FIGS. 7C and 7D will now be discussed with reference to the intensity distributions at those planes. The following discussion will be with reference to the geometrical configuration wherein the beams are offset by about 1.5 cm from the central axis.

FIG. 8A is a plot, taken in a plane perpendicular to the central axis of the system at a distance along the beam axes of about 15 cm (corresponding to FIG. 7C) showing the interaction of the beams from transducers 10a-f. This distance represents a distance wherein the beams have converged to sufficient proximity to begin cooperatively heating a cylindrical volume of tissue. Intersection points 100a-f lie generally on a 6-cm diameter circle 105. The intensity distribution of each transducer, as discussed above, is characterized by a central (on-axis) peak and a satellite peak. Within the plane of FIG. 8A, the central peaks are centered at points 100a-f while the satellite peaks have their maxima on circles 107a-f. The radius of circle 105 is close to the spacing between the central peak and its respective satellite peak. Accordingly, each central peak is enhanced by the satellite peaks of the two neighboring beams, resulting in regions of enhancement 110a-f, while all the satellite peaks reinforce one another in a region 112 surrounding the central axis of the system.

FIG. 8B is an intensity distribution taken along a diametric line 8B—8B passing through points 100a and 100d, showing the transverse intensity distributions and the manner of reinforcement in the central region. Thus it can be seen that as the beams come into proximity with one another, the central peaks are effective to heat the periphery of a cylindrical volume while the satellite peaks heat the central portion of the cylindrical volume. Approximately 50% of the beam total energy lies outside circle 105, but it is sufficiently spread out (the energy density is sufficiently low) that heating outside the 6-cm diameter is minimal.

FIGS. 9A and 9B are plots corresponding to FIGS. 8A and 8B, but for an axial distance of about 22 cm at which the beams have already passed through their points of closest approach to the central axis and begun to diverge. This corresponds to FIG. 7D. At this distance, the central peaks are centered at points 102a–f which are located within the 6-cm diameter cylindrical volume, and cause heating thereof, while the satellite peaks have diminished in relative intensity to such a degree that they do not make a major contribution to the heating.

It is noted that the intensity plots of FIGS. 4A–B, 5A–B, 6, 8A–B, and 9A–B do not take into account the attenuation factor caused by the passage of the beam through the subject tissue volume. This attenuation factor amounts to approximately 10%/cm. Thus, there is an attenuation of about 50% as the beam propagates from 15 cm to 22 cm, but at 22 cm, about 85–90% of the energy is within the cylindrical region. Thus, as the beams move through the tissue, the attenuation is offset by an increased percentage of the remaining power being transferred inside the desired region. As a result of this transfer compensation and the thermal diffusion characteristics of perfused tissue, relatively uniform temperature distribution is sustained through the volume. FIG. 10 is a plot showing isotherms (lines of constant temperature) for a subject volume of perfused tissue. It can be seen that the heating is surprisingly uniform over a rather large generally cylindrical volume, with a temperature above 42.5° C. being maintained within a volume of diameter approximately 5 cm and axial length approximately 5 cm.

It is noted that the attenuation is inherent in any individual transducer field configuration and any multiple transducer arrangement. The present invention still allows a proportionately greater amount of power to be delivered to the far field region without appreciable heating of the near field region. Moreover, the attenuation is helpful in the sense that it provides for rapid falloff beyond the region of beam convergence.

The volume of the heated region may be controlled by varying the convergence angle of the beams relative to the common axis. Moreover, since the transition distance increases with an increase in either the crystal diameter or the frequency while the width of the central peak decreases with an increase of either diameter or frequency, it is possible to achieve desired combinations that can lead to a desired heated volume. It should be noted, the central transducer may be designed to supply heat as well as ranging, thereby increasing possible combinations.

The present invention provides an instrumentality for heating discrete regions of a subject tissue volume, and is capable of achieving specified temperatures within a desired range. It is, of course, a matter for the particular treatment protocol to define the desired temperatures and times. For the system described above, a treatment time of about 30 minutes is typical. While the precise mechanism by which and conditions under which hyperthermia has utility in the treatment of tumors is not understood, it appears that the effect is more rapidly achieved if the tumor is heated to higher temperatures, the required treatment time being generally inversely proportional to the temperature change. Rapid heating has the advantage that perfusion is no longer a major factor in determining final temperatures so that a small volume may be precisely controlled and confined and then the small volume may be used ultimately to provide hyperthermia treatment for a larger volume by sweeping the small volume throughout the large volume. The rapid heating of a small volume is best achieved by aligning the transducer axes so that they actually intersect each other (and typically the central axis) at a common point so that the central peaks overlap. It might appear at first glance that the suppression of the near field peak intensity would be less important in this application where the heated small region is moved about. However, it must be remembered that the spatial translation of the beams in the near field region is small, so the same region of intervening tissue is subjected to the passage of the beams even as the intensely heated small region is moved about.

In summary, it can be seen that the present invention provides an ultrasonic hyperthermia system capable of heating deep-seated tissue regions, thus rendering possible treatment of deep-seated tumors without appreciable heating of the tissues outside the region of interest. The degree of control with which the heating may be carried out renders the present invention highly suitable for use in correlation with a computerized tomography scan which could even more precisely take into account irregular shapes.

While the above provides a full and complete disclosure of the preferred embodiment of the present invention, various modifications, alternate constructions, and equivalents may be employed without departing from the true spirit and scope of the invention. For example, convergence of the multiple beams is shown as being achieved by mounting the transducers to a concave alignment plate. It will be appreciated that such convergence could equally well be achieved by mounting the transducers more obliquely with respect to an alignment plate of any convenient surface contour to achieve a desired degree of convergence. Indeed, all the beams need not converge in the same region, but rather the degree of convergence may be varied among the beams, to achieve desired heating patterns.

Additionally, while the suppression of the near field peak is shown as being achieved by designing the transducer so that the transverse mode suppresses the compressional mode in the central region, it is also possible to achieve a similar suppression by placing strong absorber material immediately adjacent the central portion of the crystal or by utilizing a different crystal configuration, although such approaches would still require control of the effects of the transverse mode.

Moreover, while the emphasis above has been with reference to hyperthermia for tumor treatment purposes, the present invention may be used as a non-invasive surgical technique to necrotize tissue or to sterilize chronic infection sites. Therefore, the above description and illustrations should not be construed as limiting the scope of the invention which is defined by the appended claims.

What is claimed is:
1. A method of ultrasonically heating a subject volume comprising the steps of:

providing a transducer;

acoustically coupling a surface of the transducer to the subject volume; and exciting vibrations within the transducer so that compressional mode vibrations are suppressed over a generally central region of the surface;

the suppression of compressional mode vibrations providing an intensity pattern characterized by relatively low intensities in the regions of the subject volume at depths extending out to a transition distance, with a relatively high intensity on-axis peak in a region beyond the transition distance whereupon a discrete portion of the subject volume may be subjected to considerable heating without appreciable heating of the intervening portions.

2. The method of claim 1 wherein said exciting step includes the substeps of:

exciting compressional and transverse modes of vibration within the transducer; and selecting the frequency of vibration relative to the transducer size and velocity properties such that the transverse mode reduces the compressional vibration over the generally central region of the surface.

3. The method of claim 2, and further comprising the step of modulating the frequency over a range including the selected frequency to compensate for transducer imperfections.

4. A method of ultrasonically heating a discrete region within a subject volume at a substantial depth therein comprising the steps of:

providing a transducer;

acoustically coupling a surface of the transducer to the subject volume; and exciting compressional vibrations over a generally annular region of the area for propagation into the subject volume;

the dimensions of the annular region and the wavelength of ultrasonic vibrations within the subject volume defining a transition distance such that the transverse intensity distributions within the subject volume at depths greater than the transition distance display central high intensity peaks while the transverse intensity distributions within the subject volume at depths less than the transition distance are characterized by the substantial reduction of high peak intensities.

5. The method of claim 4 wherein said providing step comprises the step of providing a transducer having a contiguous surface including the annular surface region and further including a central region, and wherein said exciting step comprises the substeps of exciting compressional vibrations over the annular region and central region and inducing transverse mode vibrations to suppress the compressional vibrations in the central region.

6. Apparatus for ultrasonically heating a subject volume comprising:

a transducer;

means for acoustically coupling a surface of said transducer to said subject volume; and electrical drive means for applying an alternating voltage to said transducer, thereby exciting vibrations within said transducer so that compressional mode vibrations are induced in said transducer and propagated into said subject volume;

said drive means being operable to apply said alternating voltage at a frequency which causes the compressional mode vibrations to be suppressed over a generally central region of the surface, the suppression of compressional mode vibrations providing an intensity distribution characterized by relatively low intensities in the regions of said subject volume at depths extending out to a transition distance, with a relatively high intensity on-axis peak in a region beyond said transition distance whereupon a discrete portion of said subject volume may be subjected to considerable heating without appreciable heating of the intervening portions.

7. The invention of claim 6 wherein said transducer surface is substantially flat.

8. The invention of claim 6, and further comprising means for modulating the output frequency of said drive means over a range of frequencies.

9. Apparatus for ultrasonically heating a discrete region within a subject volume at a substantial depth therein comprising:

a plurality of transducer assemblies, each of said transducer assemblies comprising a transducer adapted to be acoustically coupled to said subject volume, and associated drive means for exciting ultrasonic vibrations within said transducer so that when said transducer is acoustically coupled to said subject volume, the vibrations of said transducer cause ultrasonic waves to be propagated into said subject volume, said ultrasonic waves being characterized by an intensity pattern wherein the intensity is relatively low in the regions of the subject volume at depths extending out to a transition distance and wherein the transverse intensity distributions in the regions beyond the transition distance have relatively high intensity peaks; and means for orienting said transducers so that their axes converge toward a central axis into a small region in said subject volume.

10. The invention of claim 9 wherein said small region is near the transition distance corresponding to at least one of said transducers.

11. The invention of claim 9 wherein the intensity pattern for each of said transducers is such that the transverse intensity distributions at depths extending out to the transition distance show pronounced satellite peaks, and wherein said orienting means directs the transducer axes such that each transducer axis passes but does not cross the central axis, the cooperation of said satellite peaks and said central peaks causing heating of a volume surrounding said small region.

12. The invention of claim 9 wherein the transition distances for said transducers are substantially equal, wherein said small region includes a common point of convergence for localized heating, and wherein said transducers are mounted at generally equal distances from said common point.

13. The invention of claim 9 wherein each of said transducer assemblies is configured to produce compressional vibrations over a generally annular region of the transducer in order to suppress high intensity peaks at depths extending out to said transition distance.

14. The invention of claim 9 wherein each of said transducers has a flat surface for coupling to said subject volume.

15. The invention of claim 9 wherein said orienting means comprises:
   a concave plate; and
   means for mounting said transducers to said concave plate.

16. A method of ultrasonically heating a discrete region within a subject volume at a substantial depth therein comprising steps of:
   providing a plurality of transducer assemblies, each transducer assembly having an associated transducer;
   acoustically coupling a surface of each of the transducers to the subject volume;
   exciting vibrations within each transducer so that compressional mode vibrations are suppressed over a generally central region of the surface of each transducer;
   the suppression of compressional mode vibrations providing an intensity pattern characterized by relatively low intensities in the regions of the subject volume at depths extending out to a transition distance and further characterized by transverse intensity distributions beyond the transition distance exhibiting relatively high intensity peaks; and
   orienting said transducers so that the respective axes of the respective directions of vibration propagation generally converge toward a central axis into a small region within the subject volume.

17. The invention of claim 16 wherein said small region is near the transition distance corresponding to at least one of the transducers.

18. The method of claim 16 wherein said exciting step is carried out such that the transverse intensity distributions at depths less than the transition distance exhibit satellite peaks.

19. The method of claim 18 wherein said orienting step is carried out so that the respective axes pass but do not cross the central axis in the small region.

* * * * *